United States Patent
Noddin et al.

(10) Patent No.: US 8,936,567 B2
(45) Date of Patent: Jan. 20, 2015

(54) BALLOON BIFURCATED LUMEN TREATMENT

(75) Inventors: Richard Noddin, Elk River, MN (US); Dan Quillin, Eden Prairie, MN (US); Daniel J. Horn, Shoreview, MN (US); Ying Xiong, Lino Lakes, MN (US); Richard Goodin, Blaine, MN (US); The Thomas Trinh Tran, Coon Rapids, MN (US); Yousef F. Alkhatib, Maple Grove, MN (US); Steve Hoff, Elk River, MN (US); Richard Dunn, Brooklyn Park, MN (US); Thomas Holman, Princeton, MN (US); Zach Tegels, Minneapolis, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 416 days.

(21) Appl. No.: 12/479,611

(22) Filed: Jun. 5, 2009

(65) Prior Publication Data

US 2010/0114018 A1    May 6, 2010

Related U.S. Application Data

(60) Provisional application No. 61/059,250, filed on Jun. 5, 2008.

(51) Int. Cl.
*A61M 31/00* (2006.01)
*A61M 37/00* (2006.01)
(Continued)

(52) U.S. Cl.
CPC ............ *A61F 2/954* (2013.01); *A61M 25/1027* (2013.01); *A61F 2/958* (2013.01); *A61F 2/856* (2013.01); *A61F 2250/0036* (2013.01)
USPC .... 604/103.06; 264/523; 264/540; 604/96.01

(58) Field of Classification Search
CPC ............ A61M 25/10; A61M 25/1011; A61M 25/1027; A61M 25/1029; A61M 25/1031; A61M 25/1036; A61M 2025/1002; A61M 2025/1004; A61M 2025/1031; A61M 2025/1045; A61M 2025/1059; A61M 2025/1086; A61M 2025/1088; A61M 2025/109; A61F 2250/0036; A61F 2/954; A61F 2/958; A61F 2/856
USPC ............ 604/101.01–101.05, 103.06–103.14, 604/916, 919; 264/514, 519, 523, 540, 264/DIG. 33, 303, 527; 425/528–534, 577
See application file for complete search history.

(56) References Cited

U.S. PATENT DOCUMENTS

| | | |
|---|---|---|
| 1,596,754 A | 8/1926 | Moschelle |
| 3,657,744 A | 4/1972 | Ersek |

(Continued)

FOREIGN PATENT DOCUMENTS

| | | |
|---|---|---|
| CA | 2318314 | 7/1999 |
| DE | 9014845.2 | 1/1991 |

(Continued)

OTHER PUBLICATIONS

U.S. Appl. No. 12/479,632 to Richard Dunn et al., filed Jun. 5, 2009.
(Continued)

*Primary Examiner* — Quynh-Nhu H Vu
*Assistant Examiner* — Jenna Zhang
(74) *Attorney, Agent, or Firm* — Seager, Tufte & Wickhem LLC

(57) ABSTRACT

Balloon systems for treating bifurcated lumens include desirable burst and folding characteristics. In some cases, the balloon systems can be formed by varying the wall thickness of a balloon parison.

4 Claims, 14 Drawing Sheets

(51) Int. Cl.
    *A61F 2/954*     (2013.01)
    *A61M 25/10*     (2013.01)
    *A61F 2/958*     (2013.01)
    *A61M 29/00*     (2006.01)
    *B29C 39/02*     (2006.01)
    *B29C 43/02*     (2006.01)
    *B29C 45/00*     (2006.01)
    *B29C 47/00*     (2006.01)
    *B29C 49/00*     (2006.01)
    *B29C 49/08*     (2006.01)
    *B29C 67/00*     (2006.01)
    *B29D 22/00*     (2006.01)
    *A61F 2/856*     (2013.01)

(56) References Cited

U.S. PATENT DOCUMENTS

| | | |
|---|---|---|
| 3,872,893 A | 3/1975 | Roberts |
| 4,140,126 A | 2/1979 | Choudhury |
| 4,309,994 A | 1/1982 | Grunwald |
| 4,410,476 A | 10/1983 | Redding et al. |
| 4,413,989 A | 11/1983 | Schjeldahl et al. |
| 4,421,810 A | 12/1983 | Rasmussen |
| 4,453,545 A | 6/1984 | Inoue |
| 4,479,497 A | 10/1984 | Fogarty et al. |
| 4,503,569 A | 3/1985 | Dotter |
| 4,552,554 A | 11/1985 | Gould et al. |
| 4,681,570 A | 7/1987 | Dalton |
| 4,689,174 A | 8/1987 | Lupke |
| 4,731,055 A | 3/1988 | Melinyshyn et al. |
| 4,733,665 A | 3/1988 | Palmaz |
| 4,739,662 A | 4/1988 | Foote |
| 4,759,748 A | 7/1988 | Reed |
| 4,762,128 A | 8/1988 | Rosenbluth |
| 4,769,029 A | 9/1988 | Patel |
| 4,819,664 A | 4/1989 | Nazari |
| 4,872,874 A | 10/1989 | Taheri |
| 4,878,495 A | 11/1989 | Grayzel |
| 4,896,670 A | 1/1990 | Crittenden |
| 4,900,314 A | 2/1990 | Quackenbush |
| 4,906,244 A | 3/1990 | Pinchuk et al. |
| 4,909,258 A | 3/1990 | Kuntz et al. |
| 4,911,711 A | 3/1990 | Telfair et al. |
| 4,941,877 A | 7/1990 | Montano, Jr. |
| 4,946,464 A | 8/1990 | Pevsner |
| 4,957,501 A | 9/1990 | Lahille et al. |
| 4,957,508 A | 9/1990 | Kaneko et al. |
| 4,963,313 A | 10/1990 | Noddin et al. |
| 4,964,850 A | 10/1990 | Bouton et al. |
| 4,983,167 A | 1/1991 | Sahota |
| 4,994,071 A | 2/1991 | MacGregor |
| 5,042,976 A | 8/1991 | Ishitsu et al. |
| 5,054,501 A | 10/1991 | Chuttani et al. |
| 5,059,177 A | 10/1991 | Towne et al. |
| 5,061,240 A | 10/1991 | Cherian |
| 5,064,435 A | 11/1991 | Porter |
| 5,085,664 A | 2/1992 | Bozzo |
| 5,102,403 A | 4/1992 | Alt |
| 5,102,417 A | 4/1992 | Palmaz |
| 5,104,404 A | 4/1992 | Wolff |
| 5,117,831 A | 6/1992 | Jang et al. |
| 5,122,125 A | 6/1992 | Deuss |
| 5,135,536 A | 8/1992 | Hillstead |
| 5,147,317 A | 9/1992 | Shank et al. |
| 5,147,385 A | 9/1992 | Beck et al. |
| 5,156,785 A | 10/1992 | Zdrahala |
| 5,159,920 A | 11/1992 | Condon et al. |
| 5,192,297 A | 3/1993 | Hull |
| 5,195,970 A | 3/1993 | Gahara |
| 5,195,984 A | 3/1993 | Schatz |
| 5,211,683 A | 5/1993 | Maginot |
| 5,217,440 A | 6/1993 | Frassica |
| 5,222,971 A | 6/1993 | Willard et al. |
| 5,226,913 A | 7/1993 | Pinchuk |
| 5,234,457 A | 8/1993 | Andersen |
| 5,236,446 A | 8/1993 | Dumon |
| 5,257,974 A | 11/1993 | Cox |
| 5,263,932 A | 11/1993 | Jang |
| 5,304,220 A | 4/1994 | Maginot |
| 5,306,246 A | 4/1994 | Sahatjian et al. |
| 5,320,605 A | 6/1994 | Sahota |
| 5,324,257 A | 6/1994 | Osborne et al. |
| 5,334,153 A | 8/1994 | McIntyre et al. |
| 5,337,733 A | 8/1994 | Bauerfeind et al. |
| 5,338,300 A | 8/1994 | Cox |
| 5,342,295 A | 8/1994 | Imran |
| 5,342,297 A | 8/1994 | Jang |
| 5,342,387 A | 8/1994 | Summers |
| 5,350,395 A | 9/1994 | Yock |
| 5,382,472 A | 1/1995 | Yanidis et al. |
| 5,383,892 A | 1/1995 | Cardon et al. |
| 5,387,235 A | 2/1995 | Chuter |
| 5,395,332 A | 3/1995 | Resseman et al. |
| 5,395,334 A | 3/1995 | Keith et al. |
| 5,404,887 A | 4/1995 | Prather |
| 5,409,458 A | 4/1995 | Khairkhahan et al. |
| 5,413,581 A | 5/1995 | Goy |
| 5,413,586 A | 5/1995 | Dibie et al. |
| 5,417,208 A | 5/1995 | Winkler |
| 5,425,765 A | 6/1995 | Tiefenbrun et al. |
| 5,437,638 A | 8/1995 | Bowman |
| 5,443,497 A | 8/1995 | Venbrux |
| 5,445,624 A | 8/1995 | Jimenez |
| 5,449,373 A | 9/1995 | Pinchasik et al. |
| 5,449,382 A | 9/1995 | Dayton |
| 5,456,666 A | 10/1995 | Campbell et al. |
| 5,456,694 A | 10/1995 | Marin et al. |
| 5,456,712 A | 10/1995 | Maginot |
| 5,456,714 A | 10/1995 | Owen |
| 5,458,572 A | 10/1995 | Campbell et al. |
| 5,458,605 A | 10/1995 | Klemm |
| 5,462,530 A | 10/1995 | Jang |
| 5,476,471 A | 12/1995 | Shifrin et al. |
| 5,489,271 A | 2/1996 | Andersen |
| 5,489,295 A | 2/1996 | Piplani et al. |
| 5,496,292 A | 3/1996 | Burnham |
| 5,505,702 A | 4/1996 | Arney |
| 5,507,768 A | 4/1996 | Lau et al. |
| 5,507,769 A | 4/1996 | Marin et al. |
| 5,514,154 A | 5/1996 | Lau et al. |
| 5,514,178 A | 5/1996 | Torchio |
| 5,522,801 A | 6/1996 | Wang |
| 5,531,788 A | 7/1996 | Dibie et al. |
| 5,545,132 A | 8/1996 | Fagan et al. |
| 5,549,553 A | 8/1996 | Ressemann et al. |
| 5,549,554 A | 8/1996 | Miraki |
| 5,562,620 A | 10/1996 | Klein et al. |
| 5,562,724 A | 10/1996 | Vorwerk et al. |
| 5,562,725 A | 10/1996 | Schmitt et al. |
| 5,562,726 A | 10/1996 | Chuter |
| 5,569,295 A | 10/1996 | Lam |
| 5,571,087 A | 11/1996 | Ressemann et al. |
| 5,575,771 A | 11/1996 | Walinsky |
| 5,575,817 A | 11/1996 | Martin |
| 5,575,818 A | 11/1996 | Pinchuk |
| 5,591,228 A | 1/1997 | Edoga |
| 5,593,442 A | 1/1997 | Klein |
| 5,607,444 A | 3/1997 | Lam |
| 5,609,605 A | 3/1997 | Marshall et al. |
| 5,609,625 A | 3/1997 | Piplani et al. |
| 5,609,627 A | 3/1997 | Goicoechea et al. |
| 5,609,629 A | 3/1997 | Fearnot et al. |
| 5,613,949 A | 3/1997 | Miraki |
| 5,613,980 A | 3/1997 | Chauhan |
| 5,613,981 A | 3/1997 | Boyle et al. |
| 5,617,878 A | 4/1997 | Taheri |
| 5,626,600 A | 5/1997 | Horzewski et al. |
| 5,628,788 A | 5/1997 | Pinchuk |
| 5,632,762 A | 5/1997 | Myler |
| 5,632,763 A | 5/1997 | Glastra |
| 5,632,772 A | 5/1997 | Alcime et al. |
| 5,634,902 A | 6/1997 | Johnson et al. |
| 5,639,278 A | 6/1997 | Dereume et al. |

(56) References Cited

U.S. PATENT DOCUMENTS

| | | |
|---|---|---|
| 5,643,340 A | 7/1997 | Nunokawa |
| 5,653,743 A | 8/1997 | Martin |
| 5,662,614 A | 9/1997 | Edoga |
| 5,669,924 A | 9/1997 | Shaknovich |
| 5,669,932 A | 9/1997 | Fischell et al. |
| 5,674,197 A | 10/1997 | van Muiden et al. |
| 5,676,696 A | 10/1997 | Marcade |
| 5,676,697 A | 10/1997 | McDonald |
| 5,679,400 A | 10/1997 | Tuch |
| 5,683,451 A | 11/1997 | Lenker et al. |
| 5,690,642 A | 11/1997 | Osborne et al. |
| 5,693,084 A | 12/1997 | Chuter |
| 5,693,086 A | 12/1997 | Goicoechea et al. |
| 5,693,088 A | 12/1997 | Lazarus |
| 5,697,971 A | 12/1997 | Fischell et al. |
| 5,707,354 A | 1/1998 | Salmon et al. |
| 5,709,713 A | 1/1998 | Evans et al. |
| 5,716,365 A | 2/1998 | Goicoechea et al. |
| 5,716,617 A | 2/1998 | Khandke et al. |
| 5,718,683 A | 2/1998 | Ressemann et al. |
| 5,718,724 A | 2/1998 | Goicoechea et al. |
| 5,720,735 A | 2/1998 | Dorros |
| 5,723,004 A | 3/1998 | Dereume et al. |
| 5,724,977 A | 3/1998 | Yock et al. |
| 5,728,158 A | 3/1998 | Lau et al. |
| 5,733,303 A | 3/1998 | Israel et al. |
| 5,735,893 A | 4/1998 | Lau et al. |
| 5,746,766 A | 5/1998 | Edoga |
| 5,749,825 A | 5/1998 | Fischell et al. |
| 5,749,848 A | 5/1998 | Jang et al. |
| 5,755,734 A | 5/1998 | Richter et al. |
| 5,755,735 A | 5/1998 | Richter et al. |
| 5,755,770 A | 5/1998 | Ravenscroft |
| 5,755,771 A | 5/1998 | Penn et al. |
| 5,755,778 A | 5/1998 | Kleshinski |
| 5,759,172 A | 6/1998 | Weber et al. |
| 5,762,631 A | 6/1998 | Klein |
| 5,776,101 A | 7/1998 | Goy |
| 5,776,161 A | 7/1998 | Globerman |
| 5,776,180 A | 7/1998 | Goicoechea et al. |
| 5,782,906 A | 7/1998 | Marshall et al. |
| 5,797,947 A | 8/1998 | Mollenauer |
| 5,800,450 A | 9/1998 | Lary et al. |
| 5,800,508 A | 9/1998 | Goicoechea et al. |
| 5,814,061 A | 9/1998 | Osborne et al. |
| 5,817,126 A | 10/1998 | Imran |
| 5,824,008 A | 10/1998 | Bolduc et al. |
| 5,824,036 A | 10/1998 | Lauterjung |
| 5,824,040 A | 10/1998 | Cox et al. |
| 5,824,041 A | 10/1998 | Lenker et al. |
| 5,824,044 A | 10/1998 | Quiachon et al. |
| 5,827,320 A | 10/1998 | Richter et al. |
| 5,833,650 A | 11/1998 | Imran |
| 5,836,966 A | 11/1998 | St. Germain |
| 5,837,008 A | 11/1998 | Berg et al. |
| 5,838,856 A | 11/1998 | Lee |
| 5,843,031 A | 12/1998 | Hermann et al. |
| 5,843,160 A | 12/1998 | Rhodes |
| 5,843,164 A | 12/1998 | Frantzen et al. |
| 5,846,204 A | 12/1998 | Solomon |
| 5,851,210 A | 12/1998 | Torossian |
| 5,851,464 A | 12/1998 | Davila et al. |
| 5,853,389 A | 12/1998 | Hijlkema |
| 5,855,600 A | 1/1999 | Alt |
| 5,855,601 A | 1/1999 | Bessler et al. |
| 5,865,178 A | 2/1999 | Yock |
| 5,868,777 A | 2/1999 | Lam |
| 5,871,536 A | 2/1999 | Lazarus |
| 5,871,537 A | 2/1999 | Holman et al. |
| 5,891,533 A | 4/1999 | Pensero et al. |
| 5,897,588 A | 4/1999 | Hull et al. |
| 5,906,640 A | 5/1999 | Penn et al. |
| 5,907,893 A | 6/1999 | Zadno-Azizi et al. |
| 5,913,895 A | 6/1999 | Burpee et al. |
| 5,913,897 A | 6/1999 | Corso, Jr. et al. |
| 5,921,958 A | 7/1999 | Ressemann et al. |
| 5,922,020 A | 7/1999 | Klein et al. |
| 5,928,248 A | 7/1999 | Acker |
| 5,938,682 A | 8/1999 | Hojeibane et al. |
| 5,938,696 A | 8/1999 | Goicoechea et al. |
| 5,948,016 A | 9/1999 | Jang |
| 5,951,599 A | 9/1999 | McCrory |
| 5,961,548 A | 10/1999 | Shmulewitz |
| 5,967,986 A | 10/1999 | Cimochowski et al. |
| 5,972,018 A | 10/1999 | Israel et al. |
| 6,007,517 A | 12/1999 | Anderson |
| 6,013,054 A | 1/2000 | Jiun Yan |
| 6,013,091 A | 1/2000 | Ley et al. |
| 6,017,324 A | 1/2000 | Tu et al. |
| 6,017,363 A | 1/2000 | Hojeibane |
| 6,024,763 A | 2/2000 | Lenker et al. |
| 6,030,414 A | 2/2000 | Taheri |
| 6,033,434 A | 3/2000 | Borghi |
| 6,033,435 A | 3/2000 | Penn et al. |
| 6,036,682 A | 3/2000 | Lange et al. |
| 6,039,749 A | 3/2000 | Marin et al. |
| 6,042,597 A | 3/2000 | Kveen et al. |
| 6,045,557 A | 4/2000 | White et al. |
| 6,048,361 A | 4/2000 | Von Oepen |
| 6,056,775 A | 5/2000 | Borghi et al. |
| 6,059,823 A | 5/2000 | Holman et al. |
| 6,059,824 A | 5/2000 | Taheri |
| 6,066,168 A | 5/2000 | Lau et al. |
| 6,068,655 A | 5/2000 | Seguin et al. |
| 6,071,285 A | 6/2000 | Lashinski et al. |
| 6,086,611 A | 7/2000 | Duffy et al. |
| 6,090,127 A | 7/2000 | Globerman |
| 6,090,128 A | 7/2000 | Douglas |
| 6,090,133 A | 7/2000 | Richter et al. |
| 6,096,073 A | 8/2000 | Webster et al. |
| 6,099,497 A | 8/2000 | Adams et al. |
| 6,117,117 A | 9/2000 | Mauch |
| 6,117,156 A | 9/2000 | Richter et al. |
| 6,126,685 A | 10/2000 | Lenker et al. |
| 6,129,738 A | 10/2000 | Lashinski et al. |
| 6,129,754 A | 10/2000 | Kanesaka et al. |
| 6,142,973 A | 11/2000 | Carleton et al. |
| 6,152,945 A | 11/2000 | Bachinski et al. |
| 6,165,195 A | 12/2000 | Wilson et al. |
| 6,165,197 A | 12/2000 | Yock |
| 6,165,214 A | 12/2000 | Lazarus |
| 6,179,867 B1 | 1/2001 | Cox |
| 6,183,506 B1 | 2/2001 | Penn et al. |
| 6,183,509 B1 | 2/2001 | Dibie |
| 6,190,403 B1 | 2/2001 | Fischell et al. |
| 6,193,746 B1 | 2/2001 | Strecker |
| 6,203,569 B1 | 3/2001 | Wijay |
| 6,210,380 B1 | 4/2001 | Mauch |
| 6,210,429 B1 | 4/2001 | Vardi et al. |
| 6,217,527 B1 | 4/2001 | Selmon et al. |
| 6,217,608 B1 | 4/2001 | Penn et al. |
| 6,221,080 B1 | 4/2001 | Power |
| 6,221,090 B1 | 4/2001 | Wilson |
| 6,221,098 B1 | 4/2001 | Wilson et al. |
| 6,231,563 B1 | 5/2001 | White et al. |
| 6,231,598 B1 | 5/2001 | Berry et al. |
| 6,231,600 B1 | 5/2001 | Zhong |
| 6,235,051 B1 | 5/2001 | Murphy |
| 6,241,762 B1 | 6/2001 | Shanley |
| 6,258,073 B1 | 7/2001 | Mauch |
| 6,258,099 B1 | 7/2001 | Mareiro et al. |
| 6,258,116 B1 | 7/2001 | Hojeibane |
| 6,258,121 B1 | 7/2001 | Yang et al. |
| 6,261,273 B1 | 7/2001 | Ruiz |
| 6,261,305 B1 | 7/2001 | Marotta et al. |
| 6,261,319 B1 | 7/2001 | Kveen et al. |
| 6,264,682 B1 | 7/2001 | Wilson et al. |
| 6,273,911 B1 | 8/2001 | Cox et al. |
| 6,273,913 B1 | 8/2001 | Wright et al. |
| 6,287,314 B1 | 9/2001 | Lee et al. |
| 6,290,673 B1 | 9/2001 | Shanley |
| 6,293,967 B1 | 9/2001 | Shanley |
| 6,299,634 B1 | 10/2001 | Bergeron |
| 6,302,906 B1 | 10/2001 | Goicoechea et al. |

(56) References Cited

U.S. PATENT DOCUMENTS

| | | |
|---|---|---|
| 6,309,412 B1 | 10/2001 | Lau et al. |
| 6,309,414 B1 | 10/2001 | Rolando et al. |
| 6,312,459 B1 | 11/2001 | Huang et al. |
| 6,325,821 B1 | 12/2001 | Gaschino et al. |
| 6,325,826 B1 | 12/2001 | Vardi et al. |
| 6,334,870 B1 | 1/2002 | Ehr et al. |
| 6,346,089 B1 | 2/2002 | Dibie |
| 6,350,278 B1 | 2/2002 | Lenker et al. |
| 6,355,060 B1 | 3/2002 | Lenker et al. |
| 6,358,266 B1 | 3/2002 | Bonutti |
| 6,361,544 B1 | 3/2002 | Wilson et al. |
| 6,361,555 B1 | 3/2002 | Wilson |
| 6,371,978 B1 | 4/2002 | Wilson |
| 6,383,213 B2 | 5/2002 | Wilson et al. |
| 6,383,215 B1 | 5/2002 | Sass |
| 6,387,120 B2 | 5/2002 | Wilson et al. |
| 6,395,018 B1 | 5/2002 | Castaneda |
| 6,398,792 B1 | 6/2002 | O'Connor |
| 6,398,804 B1 | 6/2002 | Spielberg |
| 6,428,567 B2 | 8/2002 | Wilson et al. |
| 6,428,568 B2 | 8/2002 | Gaudoin et al. |
| 6,428,570 B2 | 8/2002 | Globerman |
| 6,432,133 B1 | 8/2002 | Lau et al. |
| 6,436,104 B2 | 8/2002 | Hojeibane |
| 6,436,134 B2 | 8/2002 | Richter et al. |
| 6,468,302 B2 | 10/2002 | Cox et al. |
| 6,475,208 B2 | 11/2002 | Mauch |
| 6,478,816 B1 | 11/2002 | Kveen et al. |
| 6,482,211 B1 | 11/2002 | Choi |
| 6,485,511 B2 | 11/2002 | Lau et al. |
| 6,494,905 B1 | 12/2002 | Zedler et al. |
| 6,508,836 B2 | 1/2003 | Wilson et al. |
| 6,511,504 B1 | 1/2003 | Lau et al. |
| 6,511,505 B2 | 1/2003 | Cox et al. |
| 6,520,988 B1 | 2/2003 | Colombo et al. |
| 6,527,799 B2 | 3/2003 | Shanley |
| 6,540,719 B2 | 4/2003 | Bigus et al. |
| 6,540,779 B2 | 4/2003 | Richter et al. |
| 6,544,224 B1 * | 4/2003 | Steese-Bradley ........ 604/103.06 |
| 6,572,647 B1 | 6/2003 | Supper et al. |
| 6,579,309 B1 | 6/2003 | Loos et al. |
| 6,579,312 B2 | 6/2003 | Wilson et al. |
| 6,582,394 B1 | 6/2003 | Reiss et al. |
| 6,582,459 B1 | 6/2003 | Lau et al. |
| 6,596,020 B2 | 7/2003 | Vardi et al. |
| 6,596,022 B2 | 7/2003 | Lau et al. |
| 6,599,315 B2 | 7/2003 | Wilson |
| 6,599,316 B2 | 7/2003 | Vardi et al. |
| 6,602,284 B2 | 8/2003 | Cox et al. |
| 6,641,609 B2 | 11/2003 | Globerman |
| 6,645,241 B1 | 11/2003 | Strecker |
| 6,652,873 B2 | 11/2003 | Deaver et al. |
| 6,669,717 B2 | 12/2003 | Marotta et al. |
| 6,676,667 B2 | 1/2004 | Mareiro et al. |
| 6,679,911 B2 | 1/2004 | Burgermeister |
| 6,689,156 B1 | 2/2004 | Davidson et al. |
| 6,692,483 B2 | 2/2004 | Vardi et al. |
| 6,695,877 B2 | 2/2004 | Brucker et al. |
| 6,706,062 B2 | 3/2004 | Vardi et al. |
| 6,709,440 B2 | 3/2004 | Matin et al. |
| 6,736,841 B2 | 5/2004 | Musbach et al. |
| 6,770,092 B2 | 8/2004 | Richter |
| 6,780,174 B2 | 8/2004 | Mauch |
| 6,802,856 B2 | 10/2004 | Wilson |
| 6,827,735 B2 | 12/2004 | Greenberg |
| 6,827,736 B2 | 12/2004 | Perouse |
| 6,835,203 B1 | 12/2004 | Vardi et al. |
| 6,852,124 B2 | 2/2005 | Cox et al. |
| 6,855,125 B2 | 2/2005 | Shanley |
| 6,890,349 B2 | 5/2005 | McGuckin, Jr. et al. |
| 6,908,477 B2 | 6/2005 | McGuckin, Jr. et al. |
| 6,942,689 B2 | 9/2005 | Majercak |
| 6,962,602 B2 | 11/2005 | Vardi et al. |
| 6,989,025 B2 | 1/2006 | Burgmeier et al. |
| 7,004,963 B2 | 2/2006 | Wang et al. |
| 7,056,323 B2 | 6/2006 | Mareiro et al. |
| 7,105,019 B2 | 9/2006 | Hojeibane |
| 7,118,593 B2 | 10/2006 | Davidson et al. |
| 7,125,419 B2 | 10/2006 | Sequin et al. |
| 7,163,553 B2 | 1/2007 | Limon |
| 7,220,275 B2 | 5/2007 | Davidson et al. |
| 7,238,197 B2 | 7/2007 | Sequin et al. |
| 7,244,853 B2 | 7/2007 | Schreiber et al. |
| 7,252,679 B2 | 8/2007 | Fischell et al. |
| 7,344,557 B2 | 3/2008 | Yadin |
| 7,387,639 B2 | 6/2008 | Bourang et al. |
| 7,585,317 B2 | 9/2009 | Davidson et al. |
| 7,867,435 B2 * | 1/2011 | Tran et al. ..................... 264/532 |
| 2001/0012927 A1 | 8/2001 | Mauch |
| 2001/0016767 A1 | 8/2001 | Wilson et al. |
| 2001/0016768 A1 | 8/2001 | Wilson et al. |
| 2001/0023335 A1 * | 9/2001 | Fischell et al. ........... 604/103.07 |
| 2001/0027291 A1 | 10/2001 | Shanley |
| 2001/0027331 A1 | 10/2001 | Thompson |
| 2001/0027338 A1 | 10/2001 | Greenberg |
| 2001/0029396 A1 | 10/2001 | Wilson et al. |
| 2001/0037116 A1 | 11/2001 | Wilson et al. |
| 2001/0037138 A1 | 11/2001 | Wilson et al. |
| 2001/0037140 A1 | 11/2001 | Gaudoin et al. |
| 2001/0037146 A1 | 11/2001 | Lau et al. |
| 2001/0037147 A1 | 11/2001 | Lau et al. |
| 2001/0039395 A1 | 11/2001 | Mareiro et al. |
| 2001/0039448 A1 | 11/2001 | Dibie |
| 2001/0041927 A1 | 11/2001 | Solem |
| 2001/0047201 A1 | 11/2001 | Cox et al. |
| 2001/0049552 A1 | 12/2001 | Richter et al. |
| 2001/0056297 A1 | 12/2001 | Hojeibane |
| 2002/0013618 A1 | 1/2002 | Marotta et al. |
| 2002/0013619 A1 | 1/2002 | Shanley |
| 2002/0022874 A1 | 2/2002 | Wilson |
| 2002/0026232 A1 | 2/2002 | Marotta et al. |
| 2002/0032478 A1 | 3/2002 | Boekstegers et al. |
| 2002/0035392 A1 | 3/2002 | Wilson |
| 2002/0042650 A1 | 4/2002 | Vardi et al. |
| 2002/0052648 A1 | 5/2002 | McGuckin, Jr. et al. |
| 2002/0058990 A1 | 5/2002 | Jang |
| 2002/0072790 A1 | 6/2002 | McGuckin, Jr. et al. |
| 2002/0107564 A1 | 8/2002 | Cox et al. |
| 2002/0111675 A1 | 8/2002 | Wilson |
| 2002/0123790 A1 | 9/2002 | White et al. |
| 2002/0123797 A1 | 9/2002 | Majercak |
| 2002/0123798 A1 | 9/2002 | Burgermeister |
| 2002/0151959 A1 | 10/2002 | Von Oepen |
| 2002/0156516 A1 | 10/2002 | Vardi et al. |
| 2002/0156517 A1 | 10/2002 | Perouse |
| 2002/0165604 A1 | 11/2002 | Shanley |
| 2002/0173835 A1 | 11/2002 | Bourang et al. |
| 2002/0173840 A1 | 11/2002 | Brucker et al. |
| 2002/0177892 A1 | 11/2002 | Globerman |
| 2002/0183763 A1 | 12/2002 | Callol et al. |
| 2002/0193872 A1 | 12/2002 | Trout, III et al. |
| 2002/0193873 A1 * | 12/2002 | Brucker et al. .............. 623/1.35 |
| 2003/0004535 A1 | 1/2003 | Musbach et al. |
| 2003/0009209 A1 | 1/2003 | Hojeibane |
| 2003/0009214 A1 | 1/2003 | Shanley |
| 2003/0014102 A1 | 1/2003 | Hong et al. |
| 2003/0023301 A1 | 1/2003 | Cox et al. |
| 2003/0028211 A1 | 2/2003 | Crocker et al. |
| 2003/0050688 A1 | 3/2003 | Fischell et al. |
| 2003/0055378 A1 | 3/2003 | Wang et al. |
| 2003/0074047 A1 | 4/2003 | Richter |
| 2003/0093109 A1 | 5/2003 | Mauch |
| 2003/0114912 A1 | 6/2003 | Sequin et al. |
| 2003/0114915 A1 | 6/2003 | Mareiro et al. |
| 2003/0125791 A1 | 7/2003 | Sequin et al. |
| 2003/0125799 A1 | 7/2003 | Limon |
| 2003/0125802 A1 | 7/2003 | Callol et al. |
| 2003/0144683 A1 | 7/2003 | Sirhan et al. |
| 2003/0163148 A1 | 8/2003 | Wang et al. |
| 2004/0015227 A1 | 1/2004 | Vardi et al. |
| 2004/0072849 A1 | 4/2004 | Schreiber et al. |
| 2004/0117003 A1 | 6/2004 | Ouriel et al. |
| 2004/0133223 A1 | 7/2004 | Weber |
| 2004/0133268 A1 | 7/2004 | Davidson et al. |

(56) References Cited

U.S. PATENT DOCUMENTS

| | | |
|---|---|---|
| 2004/0138737 A1 | 7/2004 | Davidson et al. |
| 2004/0148006 A1 | 7/2004 | Davidson et al. |
| 2004/0225318 A1 | 11/2004 | Eidenschink et al. |
| 2005/0015046 A1 | 1/2005 | Weber et al. |
| 2005/0015108 A1 | 1/2005 | Williams et al. |
| 2005/0027344 A1 | 2/2005 | Eidenschink |
| 2005/0060027 A1 | 3/2005 | Khenansho et al. |
| 2005/0102019 A1* | 5/2005 | Yadin ............................ 623/1.11 |
| 2005/0102023 A1 | 5/2005 | Yadin et al. |
| 2005/0177130 A1 | 8/2005 | Konstantino et al. |
| 2006/0182873 A1* | 8/2006 | Klisch et al. .................. 427/2.1 |
| 2006/0184092 A1* | 8/2006 | Atanasoska et al. ............ 604/20 |
| 2007/0191923 A1 | 8/2007 | Weber et al. |
| 2008/0097302 A1 | 4/2008 | Chen |
| 2008/0109060 A1 | 5/2008 | Yadin |
| 2008/0114294 A1 | 5/2008 | Holman et al. |
| 2008/0125706 A1 | 5/2008 | Sutermeister et al. |
| 2008/0243221 A1* | 10/2008 | Arcand ........................ 623/1.11 |

FOREIGN PATENT DOCUMENTS

| | | |
|---|---|---|
| DE | 29701758 | 3/1997 |
| EP | 0551179 | 7/1993 |
| EP | 0646365 | 4/1995 |
| EP | 0684022 | 11/1995 |
| EP | 0804907 | 11/1997 |
| EP | 0876805 | 11/1998 |
| EP | 0884028 | 12/1998 |
| EP | 0891751 | 1/1999 |
| EP | 0897698 | 2/1999 |
| EP | 0897700 | 2/1999 |
| EP | 0904745 | 3/1999 |
| EP | 1031328 | 8/2000 |
| EP | 1031330 | 8/2000 |
| EP | 1157674 | 11/2001 |
| EP | 1254644 | 11/2002 |
| FR | 2678508 | 1/1993 |
| WO | WO 88/06026 | 8/1988 |
| WO | WO 90/13332 | 11/1990 |
| WO | WO 91/12779 | 9/1991 |
| WO | WO 92/19308 | 11/1992 |
| WO | WO 94/26180 | 11/1994 |
| WO | WO 95/08965 | 4/1995 |
| WO | WO 95/21592 | 8/1995 |
| WO | WO 96/29955 | 10/1996 |
| WO | WO 96/41592 | 12/1996 |
| WO | WO 97/09946 | 3/1997 |
| WO | WO 97/16217 | 5/1997 |
| WO | WO 97/26936 | 7/1997 |
| WO | WO 97/32544 | 9/1997 |
| WO | WO 97/33532 | 9/1997 |
| WO | WO 97/41803 | 11/1997 |
| WO | WO 97/45073 | 12/1997 |
| WO | WO 98/17204 | 4/1998 |
| WO | WO 98/19628 | 5/1998 |
| WO | WO 98/35634 | 8/1998 |
| WO | WO 98/36709 | 8/1998 |
| WO | WO 98/37833 | 9/1998 |
| WO | WO 98/44871 | 10/1998 |
| WO | WO 98/48733 | 11/1998 |
| WO | WO 98/52497 | 11/1998 |
| WO | WO 99/15103 | 4/1999 |
| WO | WO 99/17680 | 4/1999 |
| WO | WO 99/24104 | 5/1999 |
| WO | WO 99/34749 | 7/1999 |
| WO | WO 99/36002 | 7/1999 |
| WO | WO 99/39661 | 8/1999 |
| WO | WO 99/58059 | 11/1999 |
| WO | WO 99/65419 | 12/1999 |
| WO | WO 00/00104 | 1/2000 |
| WO | WO 00/12166 | 3/2000 |
| WO | WO 00/13613 | 3/2000 |
| WO | WO 00/53122 | 9/2000 |
| WO | WO 00/74595 | 12/2000 |
| WO | WO 01/21095 | 3/2001 |
| WO | WO 01/21109 | 3/2001 |
| WO | WO 01/21244 | 3/2001 |
| WO | WO 01/70299 | 9/2001 |
| WO | WO 02/068012 | 9/2002 |
| WO | WO 02/076333 | 10/2002 |
| WO | WO 02/094336 | 11/2002 |
| WO | WO 03/055414 | 7/2003 |
| WO | WO 2004/026180 | 4/2004 |
| WO | WO 2005/046757 | 5/2005 |
| WO | WO 2005/122958 | 12/2005 |
| WO | WO 2006/014631 | 2/2006 |
| WO | WO 2006/053106 | 5/2006 |
| WO | WO 2008/024220 | 2/2008 |

OTHER PUBLICATIONS

Caputo et al., "Stent Jail: A Minimum-Security Prison," The American Journal of Cardiology, vol. 77, pp. 1226-1230, Jun. 1, 1996.

Carrie et al., "'T'-Shaped Stent Placement: A Technique for the Treatment of Dissected Bifurcation Lesions," Catheterization and Cardiovascular Diagnosis, vol. 37, pp. 311-313, 1996.

Chevalier et al., "Placement of Coronary Stents in Bifurcation Lesions by the 'Culotte' Technique," The American Journal of Cardiology, vol. 82, pp. 943-949, Oct. 15, 1998.

Colombo et al., "'Kissing' Stents for Bifurcational Coronary Lesion," Catheterization and Cardiovascular Diagnosis, vol. 30, pp. 327-330, 1993.

Dichek et al., "Seeding of Intravascular Stents with Genetically Engineered Endothelial Cells," Circulation, vol. 80, No. 5, pp. 1347-1353, Nov. 1989.

Fischman et al., "A Randomized Comparison of Coronary-Stent Placement and Balloon Angioplasty in the Treatment of Coronary Artery Disease," New England Journal of Medicine, vol. 331, No. 8, pp. 496-501, Aug. 25, 1994.

Katoh et al., "New Double Wire Technique to Stent Ostial Lesions," Catheterization and Cardiovascular Diagnosis, vol. 40, pp. 400-402, 1997.

"Laser", Wikipedia, the free encyclopedia, http://en.wikipedia.org./wiki/Laser, printed Mar. 21, 2006, 11 pages.

Lewis et al., "Acute Procedural Results in the Treatment of 30 Coronary Artery Bifurcation Lesions with a Double-Wire Atherectomy Technique for Side-Branch Protection," American Heart Journal, vol. 127, No. 6, pp. 1600-1607, 1994.

Nakamura et al., "Techniques for Palmaz-Schatz Stent Deployment in Lesions with a Large Side Branch," Catheterization and Cardiovascular Diagnosis, vol. 34, pp. 353-361, 1995.

Satler et al. "Bifurcation Disease: To Treat or Not to Treat," Catheterization and Cardiovascular Interventions, vol. 50, pp. 411-412, 2000.

Serruys et al., "A Comparison of Balloon Expandable-Stent Implantation with Balloon Angioplasty in Patients with Coronary Artery Disease," The New England Journal of Medicine, vol. 331, No. 8, pp. 489-495, Aug. 25, 1994.

Yamashita et al., "Bifurcation Lesions: Two Stents Versus One Stent—Immediate and Follow-up Results," Journal of the American College of Cardiology, vol. 35, No. 5, pp. 1145-1151, Apr. 2000.

* cited by examiner

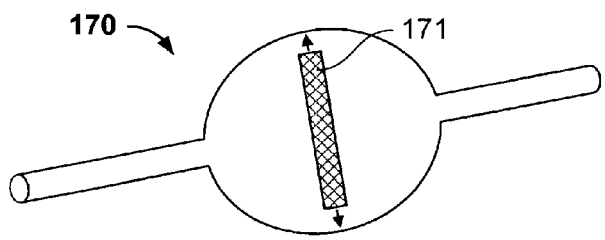
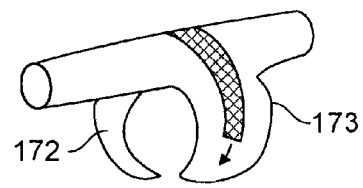
FIG. 21A      FIG. 21B
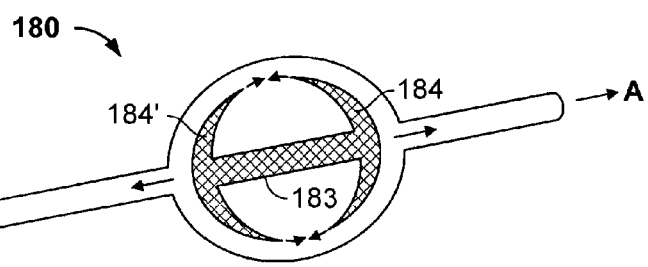
FIG. 22
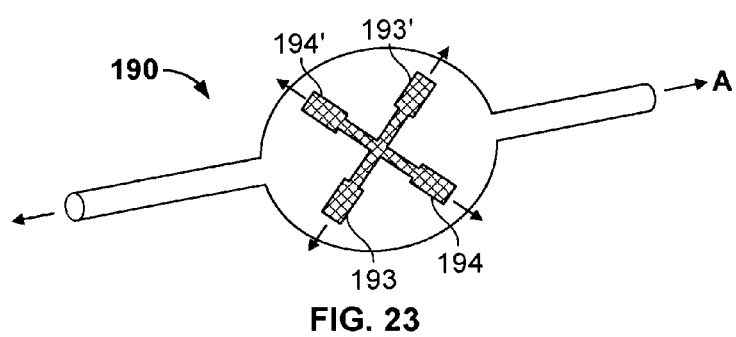
FIG. 23
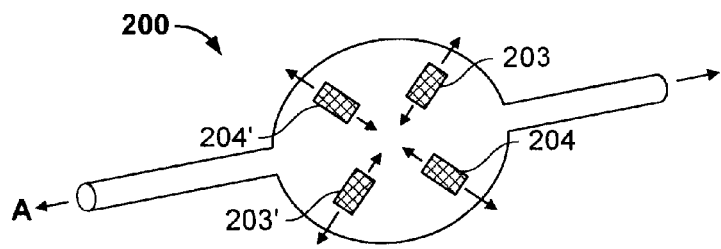
FIG. 24

BALLOON BIFURCATED LUMEN TREATMENT

CROSS REFERENCE TO RELATED APPLICATIONS

This application claims priority to U.S. Provisional Application No. 61/059,250 filed on Jun. 5, 2008, the entire contents of which is hereby incorporated by reference.

This application is related to U.S. application Ser. No. 11/599,049, filed Nov. 14, 2007, and U.S. application Ser. No. 12/479,632 filed on even date herewith, which claims the benefit of U.S. Provisional Application Ser. No. 61/059,243 filed Jun. 5, 2008, the entire contents of all of which are hereby incorporated by reference.

TECHNICAL FIELD

This disclosure relates to the treatment of bifurcated lumens with a balloon.

BACKGROUND

The body includes various passageways including blood vessels such as arteries, and other body lumens. These passageways sometimes become occluded or weakened. For example, they can be occluded by a tumor, restricted by plaque, or weakened by an aneurysm. When this occurs, the passageway can be reopened or reinforced, or even replaced, with a medical endoprosthesis. An endoprosthesis is an artificial implant that is typically placed in a passageway or lumen in the body. Many endoprostheses are tubular members, examples of which include stents, stent-grafts, and covered stents.

Many endoprostheses can be delivered inside the body by a catheter. Typically the catheter supports a reduced-size or compacted form of the endoprosthesis as it is transported to a desired site in the body, for example, the site of weakening or occlusion in a body lumen. Upon reaching the desired site, the endoprosthesis is installed so that it can contact the walls of the lumen.

One method of installation involves expanding the endoprosthesis. The expansion mechanism used to install the endoprosthesis may include forcing it to expand radially. For example, the expansion can be achieved with a catheter that carries a balloon in conjunction with a balloon-expandable endoprosthesis reduced in size relative to its final form in the body. The balloon is inflated to deform and/or expand the endoprosthesis in order to fix it at a predetermined position in contact with the lumen wall. The balloon can then be deflated, and the catheter withdrawn.

Body lumens often include bifurcated regions with branching pathways. Treatments, such as angioplasty and stent delivery, are sometimes required at locations proximate the branching physiology.

SUMMARY

The following summary is provided to facilitate an understanding of some of the innovative features unique to the present disclosure and is not intended to be a full description. A full appreciation of the disclosure can be gained by taking the entire specification, claims, drawings, and abstract as a whole.

In one embodiment, a medical device for treating a bifurcated lumen is described. The medical device may include a catheter shaft having a proximal region and a distal region, a first balloon disposed about a distal region of the catheter shaft along an axis of the catheter shaft, and a second balloon coupled to the distal region of the catheter shaft and disposed offset from the axis. The second balloon may have an expandable region configured to expand in a direction at an angle from the axis and the second balloon may have a base region opposite the expandable region, wherein the wall thickness of the base region is greater than the wall thickness of the expandable region.

In another embodiment, a medical device for treating a bifurcated lumen is described. The medical device may include a catheter shaft having a proximal region and a distal region, a first balloon disposed about a distal region of the catheter shaft along an axis of the catheter shaft, and a second balloon coupled to the distal region of the catheter shaft and disposed offset from the axis. The second balloon may have an expandable region configured to expand in a direction at an angle from the axis and a base region opposite the expandable region, wherein the second balloon includes a predefined burst region.

In another embodiment, a medical device for treating a bifurcated lumen is described. The medical device may include a catheter shaft having a proximal region and a distal region, a first balloon disposed about a distal region of the catheter shaft along an axis of the catheter shaft, and a second balloon coupled to the distal region of the catheter shaft and disposed offset from the axis. The second balloon may have an expandable region configured to expand in a direction at an angle from the axis and a base region opposite the expandable region, wherein the balloon has a predefined fold region in the base region and/or expandable region.

In other embodiment, a medical device for treating a bifurcated lumen is described. The medical device may include a catheter shaft having a proximal region and a distal region, a first balloon disposed about a distal region of the catheter shaft along an axis of the catheter shaft, and a second balloon coupled to the distal region of the catheter shaft and disposed offset from the axis. The second balloon may have an expandable region configured to expand at an angle from the axis a base region opposite the expandable region, wherein the first balloon and second balloon are concentrically disposed about the catheter shaft.

In another embodiment, a medical device for treating a bifurcated lumen is described. The medical device may include a catheter shaft having a proximal region and a distal region and a balloon coupled to the distal region of the catheter shaft. The balloon may include an electroactive polymer, wherein an exposure to an electrical current may cause the electroactive polymer to expand such that the balloon folds into lobes.

In another embodiment, a method of forming a balloon for treating a bifurcated lumen is described. The method may include providing a tubular parison defining an axis and having a variable wall thickness region, utilizing the variable wall thickness region of the parison to form a balloon inflatable off the axis, and expanding the parison to form the balloon such that a first region of the parison having a greater thickness is expanded to a greater extent than a second region of the parison having a lesser thickness.

BRIEF DESCRIPTION OF DRAWINGS

The invention may be more completely understood in consideration of the following detailed description of various illustrative embodiments of the disclosure in connection with the accompanying drawings, in which:

FIGS. 4A-7 are schematics illustrating manufacture of a parison and balloon in FIGS. 3A and 3B.

FIGS. 4A and 4B are perspective views.

FIG. 7 is a perspective view illustrating processing of the balloon parison in a blowing mold.

FIGS. 21A and 21B are top and perspective views respectively of a balloon.

FIGS. 22-24 are top views of a balloon.

DETAILED DESCRIPTION

The following detailed description should be read with reference to the drawings in which similar elements in different drawings are numbered the same. The drawings, which are not necessarily to scale, depict illustrative embodiments and are not intended to limit the scope of the invention.

Figure 1A:
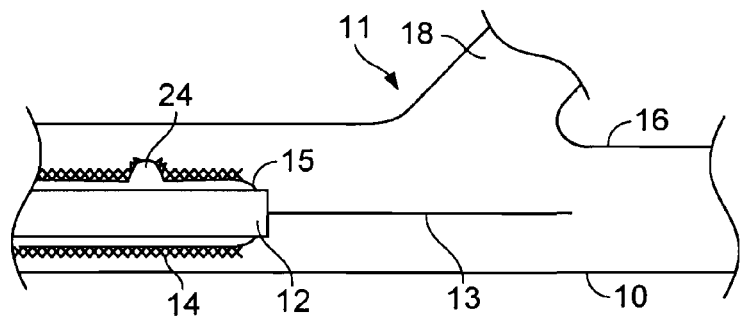
FIGS. 1A-1D are cross-sectional views illustrating delivery and deployment of a stent in a bifurcated lumen.
Figure 1B:
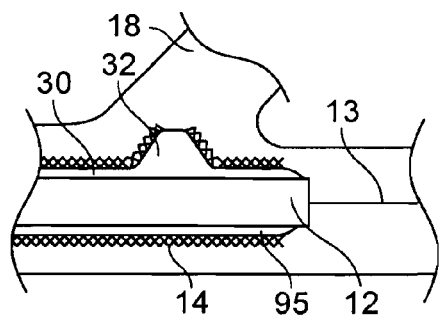
Figure 1C:
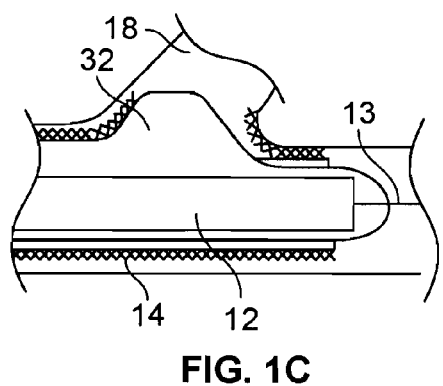
Figure 1D:
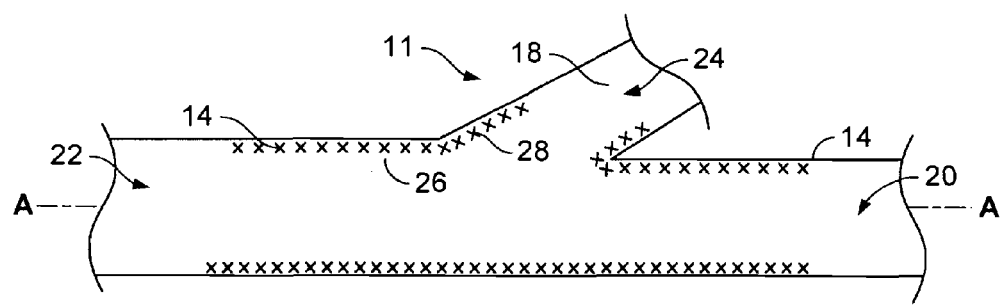

Referring to FIGS. 1A-1D, a body lumen 10, such as a blood vessel, that has a bifurcated region 11 is treated with a catheter 12 carrying a stent 14 over an inflatable balloon system 15. At the bifurcated region 11, the body lumen 10 forms a first branch 16 and a second branch 18. Referring particularly to FIG. 1A, the catheter 12 may be delivered through a tortuous pathway over a guidewire 13 to the treatment site about the bifurcated region 11. Referring as well to FIGS. 1B and 1C, the balloon system 15 is expanded to expand the stent 14 into contact with the wall of the body lumen 10. Referring to FIG. 1D, the balloon system 15 is then deflated and the catheter 12 withdrawn, leaving the stent 14 in place.

The stent 14 is arranged such that it can be placed in the bifurcated region 11. In this embodiment, the stent 14 includes distal 20 and proximal 22 openings as well as a side opening 24 such that the stent 14 will not obstruct the second branch 18 when it is positioned to span the bifurcated region in the first branch 16. In addition, the stent 14 includes a main axis region 26 which is along the axis A (shown in FIG. 1D) of the stent 14 and is expanded into contact with the first branch 16 and an off-axis region 28 that is expanded into contact with the second branch 18. The balloon system 15 likewise includes a main axis region 30, for expanding the main axis 26 of the stent, and an off-axis region 32 that expands the off-axis region 28 of the stent.

Figure 2A:
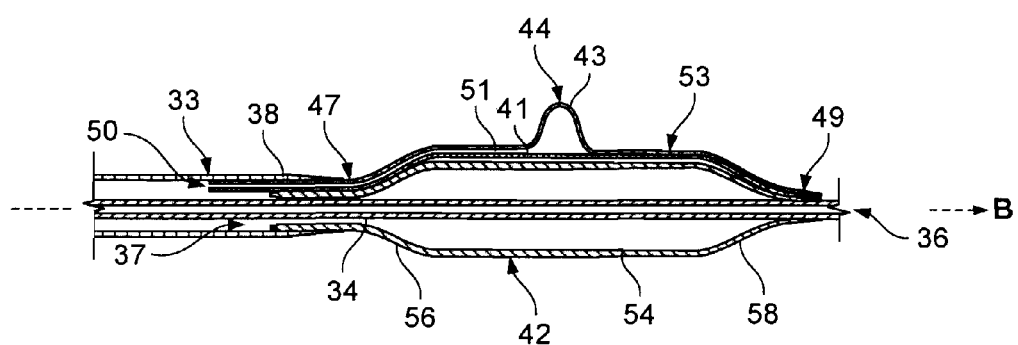
FIG. 2A is a cross-sectional view through a portion of a balloon catheter.
Figure 2B:
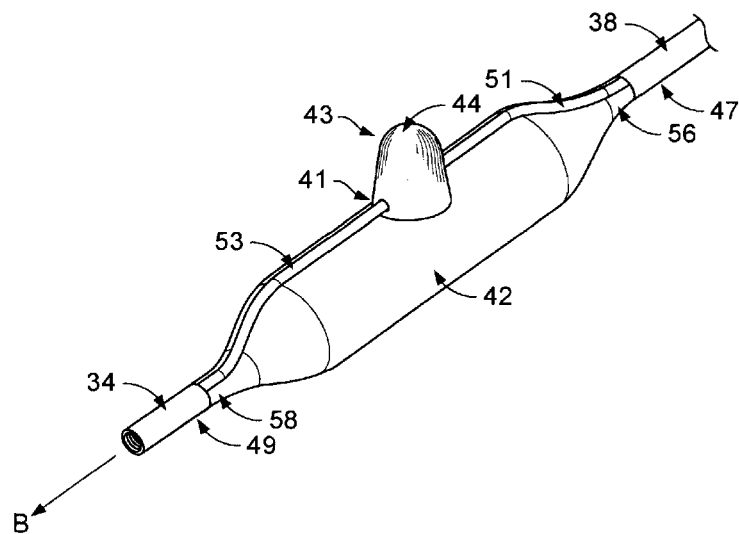
FIG. 2B is a perspective view illustrating a portion of a balloon catheter.

Referring to FIGS. 2A and 2B, a cross section and perspective view, respectively of the distal end of a balloon catheter 33 suitable for placement in a lumen 16, as in, for example, FIGS. 1A and 1B, the catheter 33 includes an inner shaft 34 defining a guidewire lumen 36, an outer shaft 38, and a dual balloon system. The concentric inner and outer shafts define an annular lumen 37 through which inflation fluid can be directed to the balloon system. The dual balloon system has a first, main balloon 42, including a region 54 that inflates into a generally cylindrical profile aligned along the axis B of the catheter to expand the stent in the first branch 16 of the lumen. The main balloon 42 also includes proximal and distal sleeves or waists 56, 58, that are attached to the catheter. The system also includes a second, off-axis balloon 44 that expands off the axis of the catheter into the second branch 18 of the lumen. The off-axis balloon 44 extends along and around a portion of the main balloon and includes a base portion 41, an apex or dome 43, and proximal and distal sleeves 51, 53. The proximal sleeves of both balloons are attached at a region 47 of outer shaft 38 and the distal sleeves of both balloons are attached to a distal region 49 of the inner shaft of the catheter. The proximal sleeve 51 or leg of the off-axis balloon 44 provides a pathway 50 for inflation fluid to the interior of the balloon 44. The distal sleeve 53 of the balloon 44 is sealed to prevent inflation fluid from passing substantially beyond the off axis inflatable portion of the balloon. In this embodiment, inflation fluid delivered through the lumen 37 is directed to the main and off-axis balloons so that the balloons are inflated substantially simultaneously. In other embodiments, the off-axis and main balloons are arranged sequentially along the catheter axis. In other embodiments, the off-axis and main balloons can be provided on separate catheters that are delivered simultaneously or sequentially. In other embodiments, a single balloon is provided that has main and off-axis inflatable regions. Exemplary stent and catheter arrangements are described in US Patent Application Publication No. 2005/0102023, and in U.S. Pat. Nos. 6,325,826; 6,210,429; 6,706,062; 6,596,020; and 6,962,602, all of which are incorporated herein by reference.

Figures 3A, 3B:
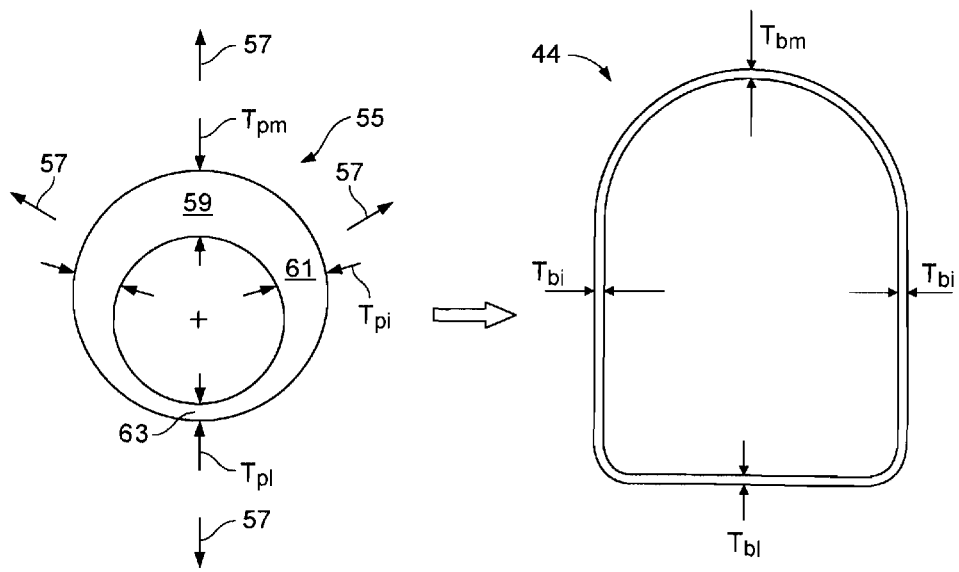
FIGS. 3A and 3B are transverse cross-sectional views through a balloon parison and a balloon wall, respectively.

Referring to FIGS. 3A and 3B, a polymer tubular parison 55 that has a variable wall thickness is used to effect a desired wall thickness in the balloon 44. Briefly, the parison 55 is oriented inside a mold that has the desired off-axis shape of the balloon. The parison 55 is then heated and pressurized from its interior to expand (arrows 57) the tubular parison 55 by radially stretching the polymer into the shape of the balloon 44. Referring particularly to FIG. 3A, the parison is formed such that its wall thickness varies with the amount of expansion that the parison will undergo during balloon formation. Referring as well to FIG. 3B, the resulting balloon has a wall thickness that is substantially uniform and predictable, thus reducing the likelihood of a thin region that could burst unpredictably. By contrast, a parison with a uniform wall thickness can result in a balloon with greater wall thickness at the base and lesser wall thickness at the dome. For example, the parison 55 has a region 59 that will undergo maximum expansion with a thickness $T_{pm}$ that is greater than a thickness in $T_{pi}$ in region 61 that undergoes intermediate expansion. The thickness of the region 61 is in turn greater than the base region 63 which has the least thickness $T_{pl}$ and undergoes the least expansion. In embodiments, the thicknesses of the balloon wall corresponding to the parison, $T_{bm}$, $T_{bi}$, and $T_{bl}$ are substantially the same. In other embodiments, the thickness $T_{bm}$ of the region of the balloon formed by maximum expansion is about 90% to 110%, e.g. 99 or 95% or more, than the region $T_{bl}$ formed by minimum expansion. In embodiments, the balloon wall thickness uniformity is ±5%, ±3% or ±1% or less. In other embodiments, variable balloon wall thicknesses can be provided, and/or defined zones having thinner wall thickness are provided to effect a desired balloon burst or folding profile, as will be described below.

Figure 4A:
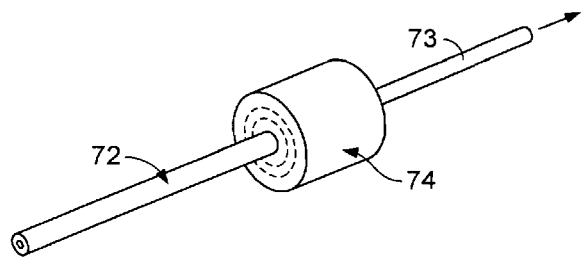
Figure 4B:
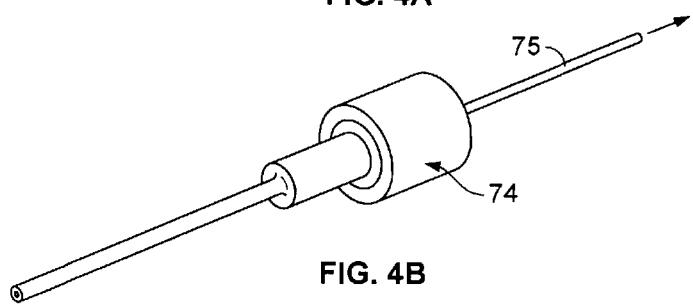
Figure 4C:
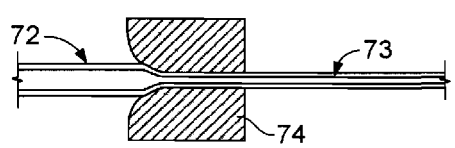
FIG. 4C is a cross-sectional view illustrating a snapshot of a process of drawing a balloon precursor tube through a die.

Referring to FIGS. 4A-7, balloon manufacture is illustrated in greater detail. Referring particularly to FIGS. 4A, 4B, and 4C, a balloon parison is formed from a length of tubing 72 that is selectively reduced in diameter. The tubing 72 can be formed by extrusion and have a substantially constant wall thickness. The ends of the tubing are reduced by drawing through a temperature-controlled die 74 to form a first reduced end 73 and a second reduced end 75.

Figure 5A:
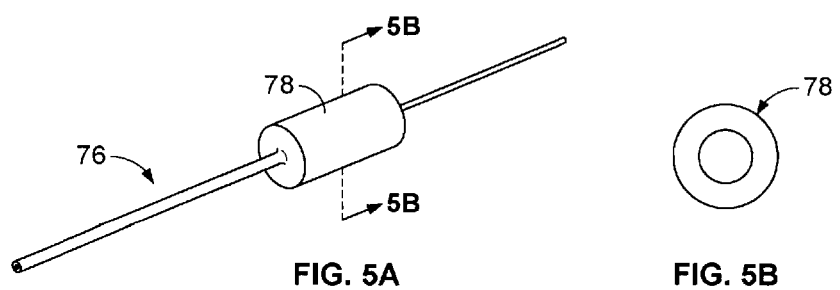
FIG. 5A is a perspective view.
Figure 5B:
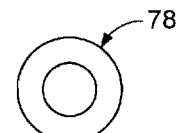
FIG. 5B is a transverse cross-sectional view (section AA in FIG. 5A) of a balloon parison.

Referring as well to FIGS. 5A and 5B, the resulting parison 76 has reduced diameter proximal and distal ends 73, 75 with a nugget 78 between the ends which will be expanded to form the off-axis inflatable portion of the balloon. Referring particularly to FIG. 5B, the wall thickness of the nugget is substantially constant about the parison axis.

Figure 6A:
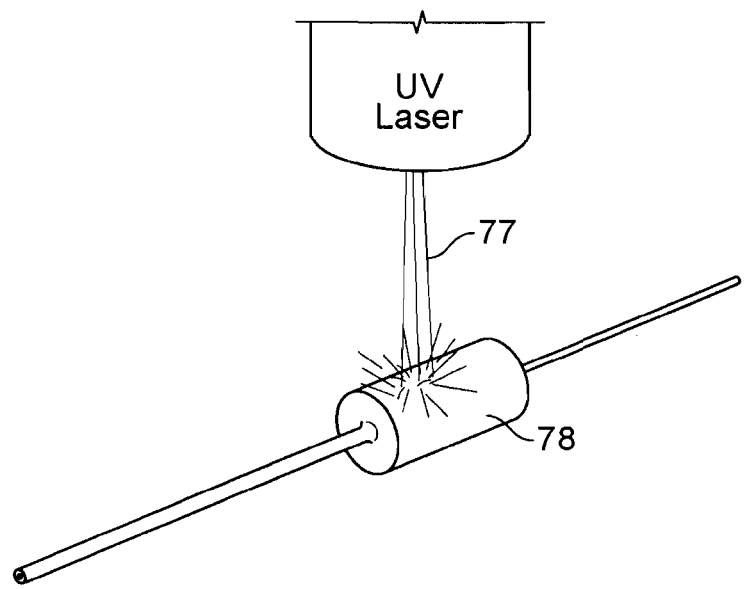
FIG. 6A is a schematic illustrating processing the balloon parison with laser radiation.
Figure 6B:
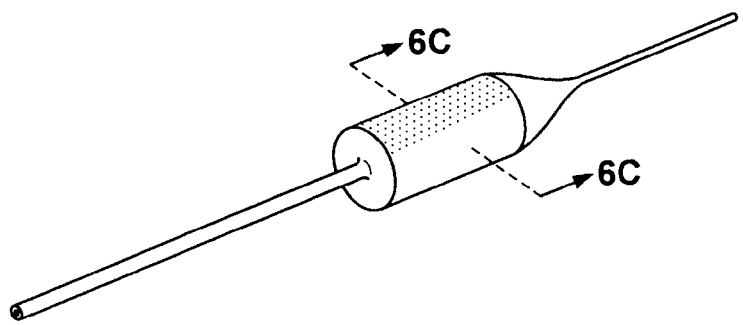
FIG. 6B is a perspective view.
Figure 6C:
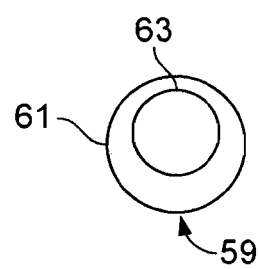
FIG. 6C is a transverse cross sectional view, (section BB in FIG. 6C) of the parison after processing.

Referring to FIGS. 6A to 6C, the parison is treated by laser irradiation to sculpt its wall thickness. Referring particularly to FIG. 6A, the laser radiation 77 is directed on to the nugget 78 to remove polymer material by ablation. A suitable laser is a UV excimer laser operating at, e.g., 193 or 240 nm. The amount of material removed can be controlled by selection of the exposure time and/or laser fluence. Laser ablation is discussed further in U.S. Pat. No. 4,911,711.

Referring particularly to FIGS. 6B and 6C, the resulting processed parison has a wall thickness profile as described above with respect to FIG. 3A, with region 59 having a greater wall thickness than region 61 and region 61 having a greater wall thickness than region 63. The inner diameter of the nugget is not modified by the ablation treatment.

Figure 7:
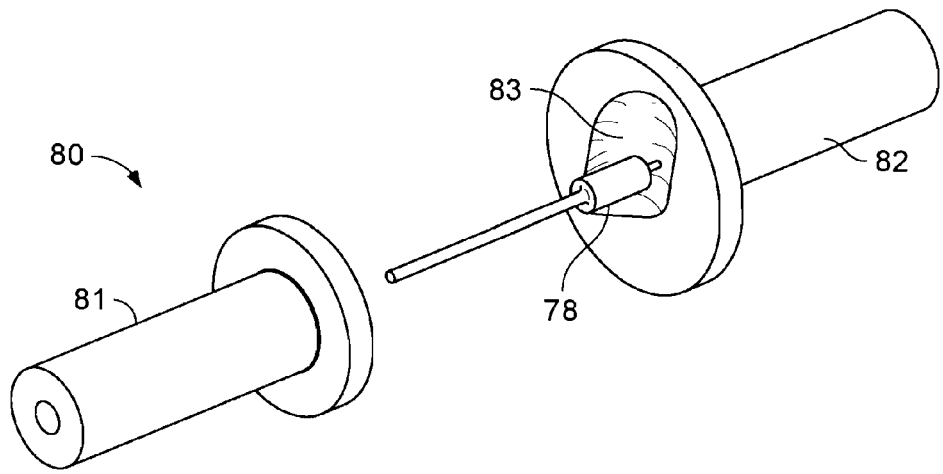

Referring to FIG. 7, the sculpted parison is then placed into a mold 80 formed of first and second halves 81, 82 which are assembled together. The mold halves 81, 82 define a chamber 83 in the desired shape of the inflatable off-axis portion of the balloon. The parison is positioned in the mold such that the nugget 78 is inside the chamber 83 and oriented such that the thicker wall regions are aligned with the region of the mold that will allow greater expansion. The mold is then heated as gas pressure is introduced to the parison so that the nugget expands into the shape of the chamber 83. The parison is then removed from the mold. The unexpanded ends of the balloon form the balloon waists. One end of the parison is sealed by collapsing it upon itself and heating to form melt seal. The other end is left open to provide a path for inflation fluid. The balloon is then attached to the catheter by melt or adhesive bonding. The proximal waist can be bonded to the proximal waist of an off-axis balloon using a mandrel to maintain the inflation fluid flowpath. The substantially unexpanded proximal waist of the off-axis balloon maintains sufficient stiffness to prevent collapse during inflation of the on-axis balloon.

Figure 8:
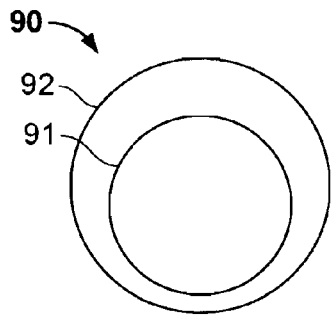
FIGS. 8-11 are end-on cross-sectional views through balloon parisons.
Figure 9:
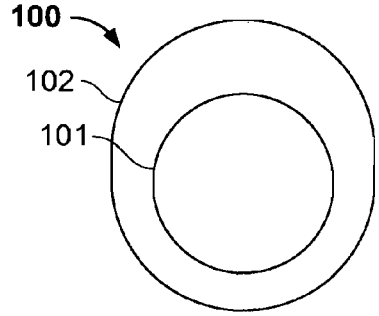
Figure 10:
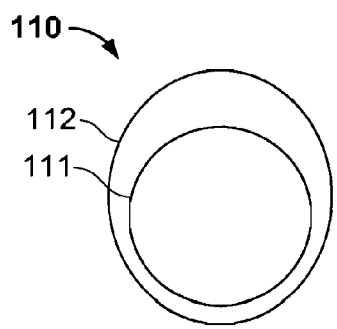
Figure 11:
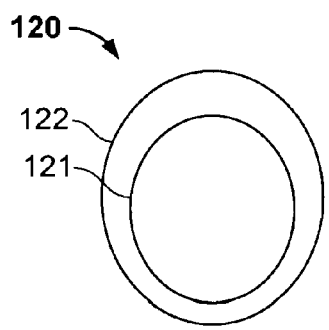

Referring to FIGS. 8-11, the thickness of the parison can be varied to produce other desired balloon profiles. Referring to FIG. 8, a parison 90 has a wall thickness that varies such that the inner 91 and outer 92 wall surfaces of the parison are both circular but at offset centers. The parison can be positioned in a mold with a circular cross-sectional profile. Referring to FIG. 9, a parison 100 has the inner wall 101 that is circular and outer wall 102 that is oval. The parison can be expanded in an elliptical mold to form an elongated oval balloon. Referring to FIG. 10, a parison 110 has an elliptical outer wall surface 111 and a circular inner wall surface 112. The parison is placed inside of an elliptical mold to form an elliptically shaped balloon. Referring to FIG. 11, the parison has inner 121 and outer 122 wall surfaces defining offset ellipses. The parison can be expanded in an elliptical mold to form an elliptical balloon. By selecting a desired inner and outer geometry, the material distribution in the resulting balloon can be controlled.

In other embodiments, the shape of the mold can match the shape of the inner surface of the parison or have a curvature between the inner and outer wall surfaces to provide fine variations in shape and wall thickness in the balloon. For example, it may be desirable to have a slightly thicker wall surface on the sides of the off-axis balloon than on the apex, since the sides of the balloon have greater engagement with the stent during expansion. In other embodiments, the parison can be shaped by techniques other than ablation. For example, the parison can be ground or shaved with a blade or the parison can be extruded to have a variable wall thickness. The balloon sleeve or waist regions of an extruded parison of variable wall thickness can be ground or laser ablated to provide a substantially constant wall thickness in these regions.

Figure 12:
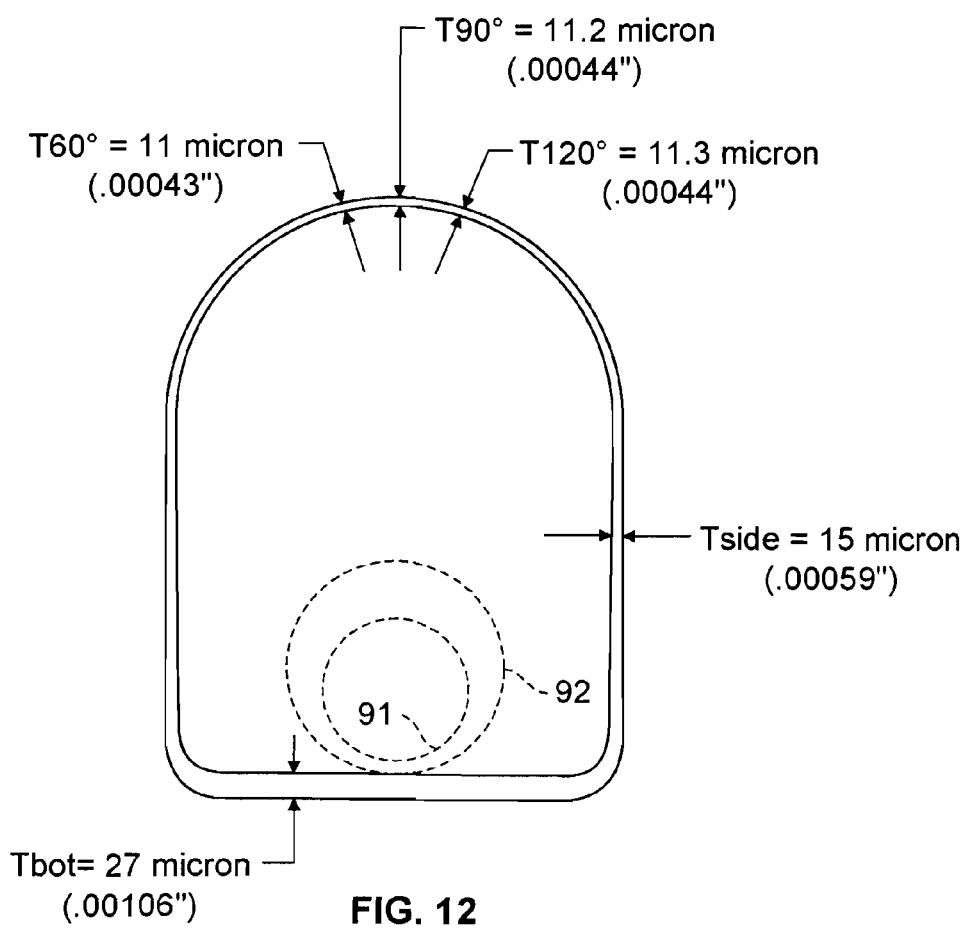
FIG. 12 is a schematic illustrating a cross-section of a balloon resulting from the balloon parison of FIG. 8.

Referring to FIG. 12, in some embodiments, a balloon formed from a parison with a profile shown in FIG. 8 results in a balloon having the following dimensions. At its bottom, the balloon has a thickness $T_{bot}$ of about 27 microns. At its side, the balloon has a thickness $T_{side}$ of about 15 microns. At its top, the balloon has a thickness $T_{90}°$ of about 11.2 microns. At its top, about 30° away from the center of the top, the balloon has a thickness $T_{60}°$ and $T_{120}°$ of about 11 and 11.3 microns, respectively. The parison had a $T_{bot}$ of about 100-130 microns before ablation and a thickness of 25-50 microns in ablated areas and a $T_{side}$ a thickness of about 25-100 microns in unablated areas (or prior to ablation) and a thickness of about 12-25 microns after ablation. The dimension of the wall thickness changes as the height of the balloon changes. The parison from which the balloon was formed had thickness dimensions of about 635 microns and about 940 microns.

Figure 13A:
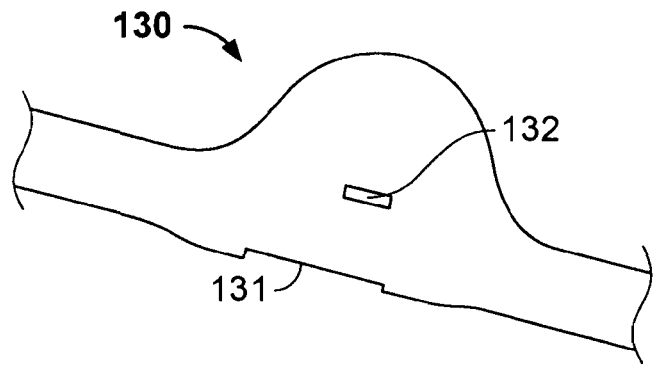
FIG. 13A is a perspective view of a balloon having preferential burst mode.
Figure 13B:
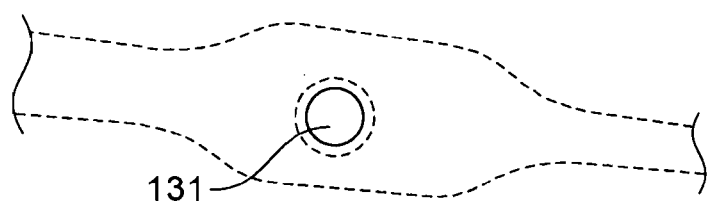
FIG. 13B is a bottom view of the balloon in FIG. 13A.

Referring as well to FIGS. 13A-13C and 14A-14C, an off-axis balloon 130 is modified to provide a selected burst profile, such that balloon burst will occur outside of the stent and side branch to reduce the likelihood the balloon will become entangled with the stent. Referring particularly to FIGS. 13A and 13B, balloon 130 includes a first preferential burst region 131 at its base and second preferential burst regions 132 in the lower region of the off-axis inflated portion.

Figure 13C:
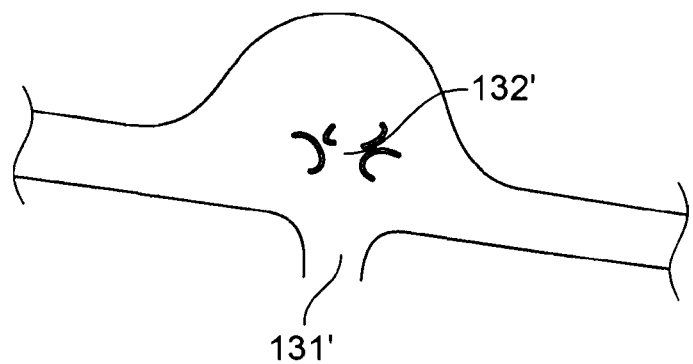
FIG. 13C is a cross-sectional view of the balloon in FIG. 13A illustrating balloon burst.
Figure 14A:
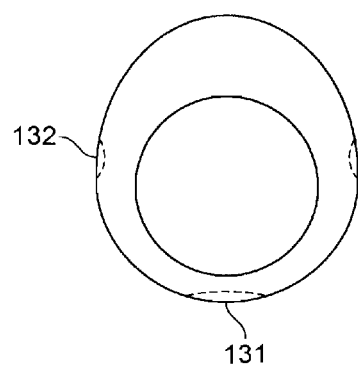
FIG. 14A is a transverse cross section of a parison for forming the balloon in FIG. 13A.
Figure 14B:
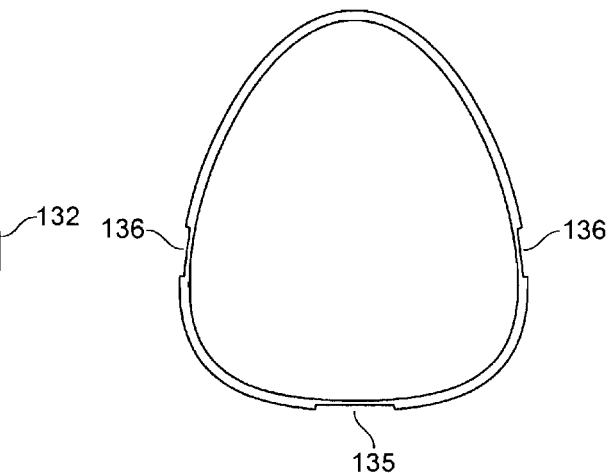
FIG. 14B is a transverse cross section of the balloon formed from the parison in FIG. 14A.
Figure 14C:
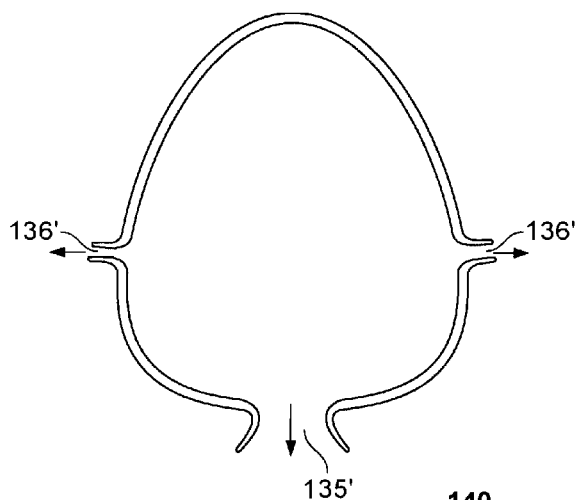
FIG. 14C is a transverse cross-sectional view illustrating balloon burst.

The preferential burst regions 131, 132 will fail before the areas outside the preferential burst regions 131, 132, creating failure regions 131', 132'. The thickness of the balloon wall in these regions is selected to fail above a given inflation pressure. Referring particularly to FIG. 13C, should the inflation pressure exceed the burst limit, the reduced thickness regions will fail before other regions of the balloon such as the regions directly engaging the stent. Referring to FIGS. 14A to 14C, the burst regions and can be formed by forming zones of reduced thickness 135, 136 in a parison 133 and then expanding the parison to form the balloon 130. The preferential burst regions 135, 136 will fail before the areas outside the preferential burst regions 131,132, creating failure regions 135', 136'. Alternatively, the zones of reduced thickness can be formed on the balloon after expanding the parison. The zones of reduced thickness can be formed by e.g. laser irradiation. In embodiments, the burst regions cover 5% or less, e.g. 1% or less of the balloon surface. In embodiments, the wall thickness of the burst regions is e.g. about 90% or less, e.g. 50-75% of the maximum wall thickness of the off-axis inflatable portion of the balloon.

Figure 15:
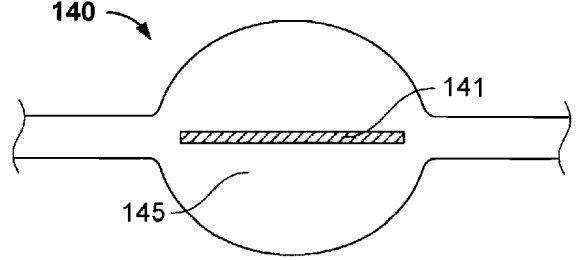
FIG. 15 is a bottom view of a balloon having a preferential folding region.
Figure 16A:
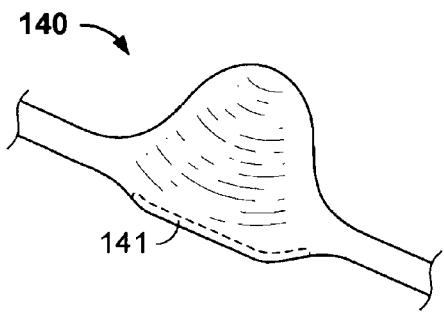
FIG. 16A is a perspective view and FIG. 16B is a transverse cross-sectional view of the balloon in FIG. 15.
Figure 16B:
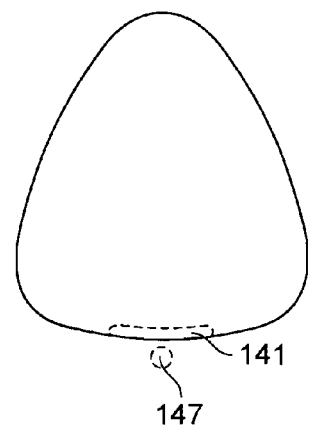
Figure 17A:
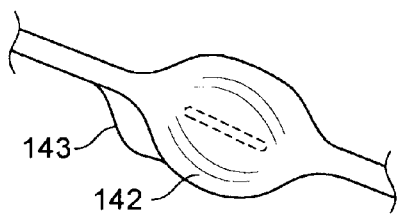
FIGS. 17A and 17B are perspective and cross-sectional views of the balloon in FIGS. 16A and 16B during an initial stage of deflation.
Figure 17B:
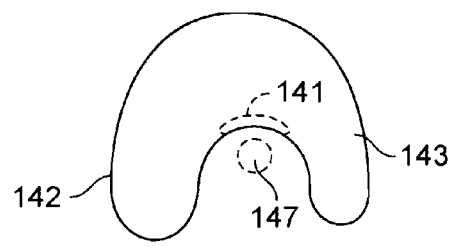
Figure 18A:
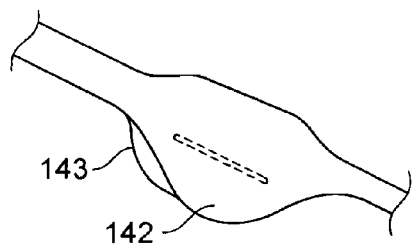
FIGS. 18A and 18B are perspective and cross-sectional views respectively of the balloon in FIGS. 17A and 17B in a further deflated condition.
Figure 18B:
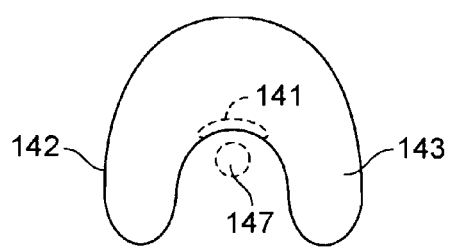

Referring to FIGS. 15-18B, a balloon 140 is such that the balloon deflates into a desired small diameter profile to facilitate removal as the catheter is withdrawn from the stent and the body. Referring particularly to FIGS. 15, 16A and 16B, the balloon 140 includes a refolding region 141 at its base 145 that has enhanced flexibility. Referring particularly to FIGS. 17A and 17B, as the inflation fluid is withdrawn from the balloon, the balloon wall folds at the region 141 to form two wing lobes 142, 143. Referring as well to FIGS. 18A and 18B, at full deflation, the balloon folds into two wings 142, 143 that provide a reduced diameter profile that facilitates withdrawal from the deflated balloon from the stent and the catheter from the lumen. As illustrated in FIGS. 16B, 17B, and 18B, the folds 142, 143 form on either side of a catheter shaft 147.

Figure 19A:
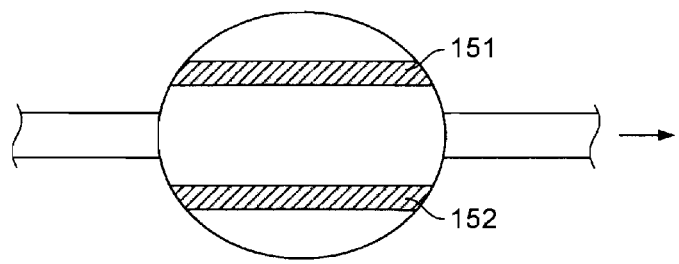
FIGS. 19A and 19B are bottom and cross-sectional views respectively of a balloon.
Figure 19B:
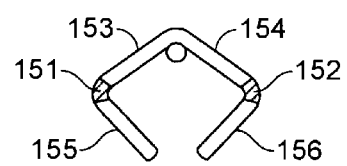
Figure 20A:
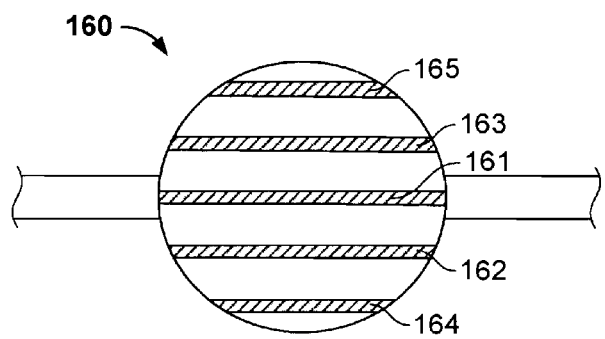
FIGS. 20A and 20B are bottom and cross-sectional views respectively of a balloon.
Figure 20B:
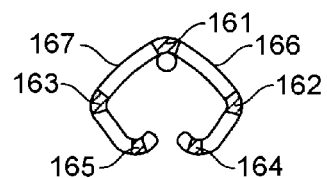

Referring to FIGS. 19A, 19B, 20A, and 20B, balloon deflation is facilitated by multiple preferential fold regions at its base. Referring particularly to FIGS. 19A and 19B, a balloon 150 has two fold regions 151, 152, which facilitate the formation of two wings 153, 154 and folding inwardly of the ends 155, 156 of the wings. Referring particularly to FIGS. 20A and 20B, a balloon 160 has five fold regions 161-165 which facilitate the formation of two lobes 166, 167 and folding inward of the two lobes.

The preferential fold regions can be formed by providing increased flexibility in the regions. The increase flexibility can be provided by reducing the wall thickness of the balloons in the fold regions, e.g. by forming reduced thickness regions in the parison, as described above, or other techniques can be utilized to vary flexibility. For example, balloon stiffness can be varied by varying the crystallinity of the polymer by exposure to heat, electromagnetic radiation, or ion beam treatments. Varying polymer flexibility is discussed in U.S. patent application Ser. No. 11/355,392, filed Feb. 16, 2006, and U.S. patent application Ser. No. 11/060,151, filed Feb. 17, 2005, both of which are incorporated herein by reference in their entirety. In embodiments, the fold regions cover 5% or less, e.g. 1% of the balloon area. For regions of reduced thickness, the regions have a thickness of about 90% or less, e.g. 50-75% of the maximum wall thickness of the off-axis inflatable portion of the balloon. In particular embodiments, the folding regions are elongated regions having a wall thickness of about 5 mm or less, e.g. 0.2 to 2 mm.

Referring to FIGS. 21A and 21B, balloon folding can also be facilitated with the use of Electro Activated Polymers (EAP's). Referring particularly to FIG. 20A, a balloon 170 includes an EAP strip 171 across the top of the off axis balloon. Referring to FIG. 20B, the EAP strip 171 is activated during deflation such that it expands (arrows), causing the balloon to fold into multiple lobes 172, 173.

Referring as well to FIGS. 22-24, the EAP strips can be configured in various patterns for various folding effects.

Referring particularly to FIG. 23, a balloon 180 on EAP 182 is provided with a linear portion 183 and two orthogonal end portions 184, 184'. When activated, the linear portion displaces the balloon along the axis A region and the end portions 184, 184', which are tapered to correspond to the curvature of the balloon, expand to fold the balloon into two lobes about the linear portion.

Referring particularly to FIG. 23, a balloon 190 includes an EAP 192 in a cross form, with enlarged ends, 193, 193', 194, 194'. When activated, the EAP expands (arrows) to fold the balloon into two lobes along the axis. The enlarged ends expand to a greater extent, enhancing the folding effect. The amount of change in dimension is proportional to the original dimension. Larger dimensions experience larger changes in dimension similar to the strain formula.

Referring to FIG. 24, a balloon 200 includes multiple EAP strips 203, 203', 204, 204'. When activated, the strips expand to fold the balloon into two lobes.

EAP's can also be utilized such that they contract when activated. The EAP's can be attached to the balloon by adhesive, melt bonding or by coextrusion. The EAP's can be selectively actuated by wires attached to the EAP's and extending along the catheter where they are attached to a source of electrical current and a controller. The wires can be directed through the catheter body and also can be embedded in the balloon polymer. Suitable EAP's are described in U.S. application Ser. No. 11/506,491, filed Aug. 18, 2006, entitled "Electrically Actuated Annelid", the entirety of which is incorporated by reference herein.

Figure 25:
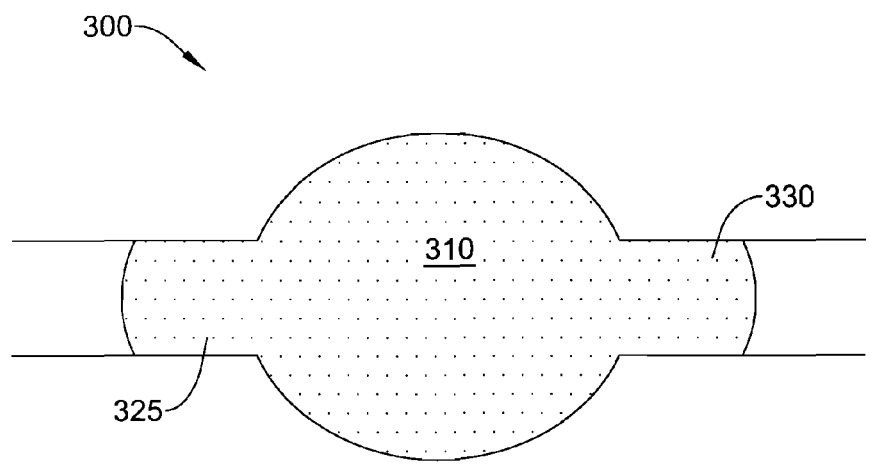
FIGS. 25-26 are perspective views of bifurcation side branch balloons that have been ablated.
Figure 26:
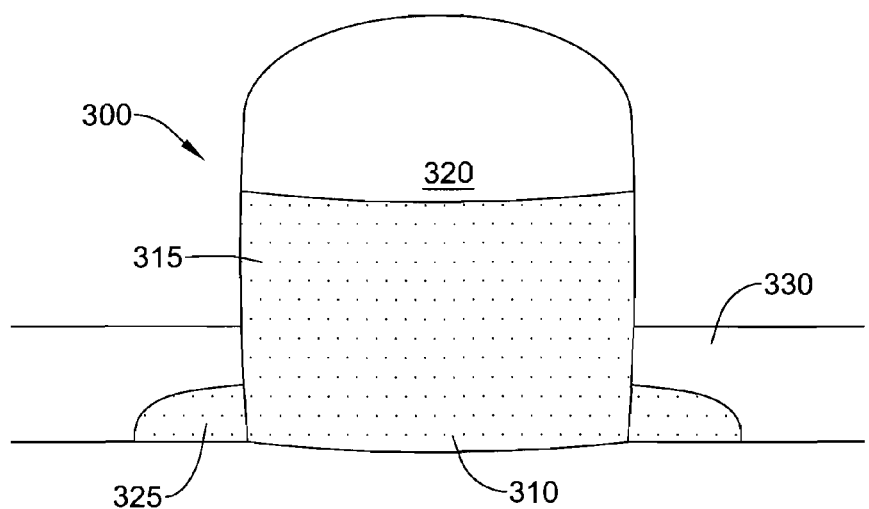

Referring to FIGS. 25 and 26, a side branch balloon 300 can be ablated, such as by using laser ablation, to reduce the amount of balloon withdrawal force from a deployed stent. Mass can be removed from the base 310 of the balloon 300 and/or from areas 315 that are adjacent to the base 310. In some embodiments, only the side branch portion 320 of the balloon is ablated. In other embodiments, both the side branch portion 320 and adjacent portions 325 of the sleeves 330 are ablated. In some embodiments, the side branch portion 320 is ablated 360° around the balloon, as shown in FIG. 26. In some embodiments, the portion of the side branch portion 320 that is furthest from the base 310 is left un-ablated. The balloon can be ablated, such as by using a UV laser operating at 193 nm using an energy setting of about 100 mJ or about 150 mJ on a balloon formed of PEBAX®. Ablating the base and adjacent portions can reduce the thickness and stiffness of the balloon, which can aid in refolding the side balloon and decreasing balloon withdrawal force.

Figure 27:
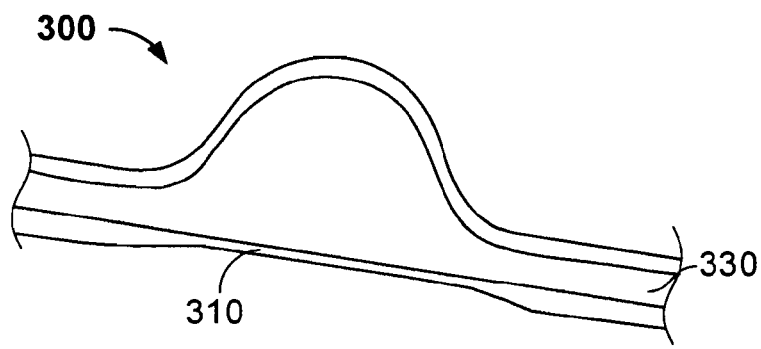
FIG. 27 shows an axial cross section of an ablated balloon.

Referring to FIG. 27, ablating the bottom of the balloon at the transition to the sleeve can produce wall thickness reduction that assists in withdrawal of the balloon from a lumen or stent. An axial cross section shows the wall thickness as being substantially uniform, except in regions of the base 310, where the wall thickness is reduced. The wall thickness is also reduced in the region where the dome transitions into the sleeves, because of having been ablated.

Suitable balloon polymers include biaxially oriented polymers, thermoplastic lastomers, engineering thermoplastic elastomers, polyethylenes, polyethylene terephthalate (PET), polybutylenes, polyamids (e.g. nylon 66), polyether block amides (e.g., PEBAX®), polypropylene (PP), polystyrene (PS), polyvinyl chlorides (PVC), polytetrafluorethylene (PTFE), polymethylmethacrylate (PMMA), polyimide, polycarbonate (PC), polyisoprene rubber (PI), nitrile rubbers, silicone rubbers, ethylene-propylene diene rubbers (EPDM), butyl rubbers (BR), thermoplastic polyurethanes (PU) (e.g., those based on a glycol ether and an isocyanate, such as PELLETHANE®). In particular embodiments, a poly(ether-amide) block copolymer having the general formula

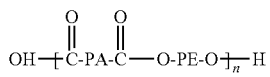

in which PA represents a polyamide segment, e.g., nylon 12, and PE represents a polyether segment, e.g., poly(tetramethylene glycol) is utilized. Such polymers are commercially available from ARKEMA under the tradename PEBAX®. The balloon can be formed of single polymer or of multiple polymers, e.g. by coextrusion. The balloon can be a multilayer balloon formed by, e.g. a coextrusion process. Balloon extrusion and blow molding are described further in Sahatjian, U.S. Pat. No. 5,306,246, "Balloon for Medical Catheter", the entirety of which is incorporated by reference herein. In embodiments, for processing PEBAX® material laser radiation at 193 nm is used. For PET, radiation of 240 nm is used. In embodiments, the balloon wall has a maximum thickness of about 0.008 inch or less, e.g. 0.003-0.007 inch and a burst strength of about 5 atm, e.g., 10 atm or more. The balloons can be used in vascular and nonvascular applications, including coronary, peripheral, carotid, esophageal or uretheral applications.

Figure 28:
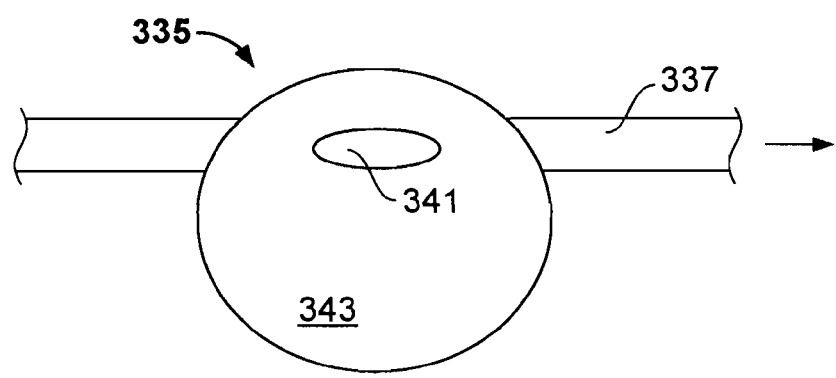
FIGS. 28-29 show bottom views of an offset side branch balloon.
Figure 29:
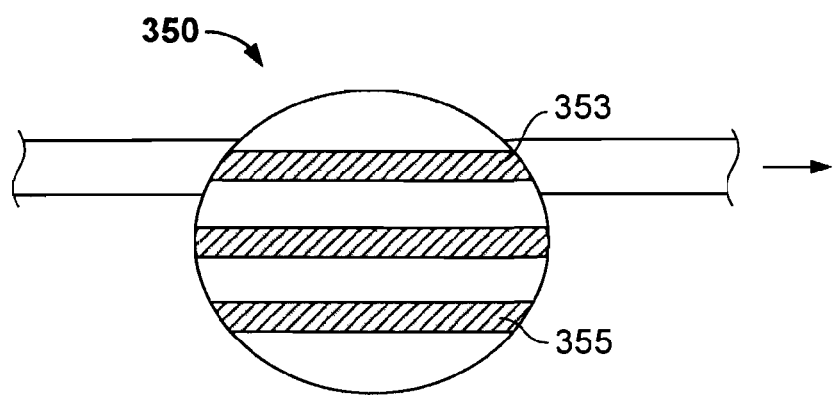

Referring to FIGS. 28 and 29, other side branch balloons can be treated to form folding regions or bursting regions. A side branch balloon 335 can have offset sleeves 337, that is, when the balloon is viewed from the top or bottom the sleeves 337 do not intersect a center of the bottom 343 of the dome. The offset sleeve side branch balloon 335 can have a burst region 341 in the lower region of the balloon. Alternatively, the burst region can be in the side of the dome, as with balloons with centered sleeves (see FIG. 13C). Alternatively, or in addition, an offset sleeve side branch balloon 350 can have folding regions 353, such as in line with the sleeve. The balloon 350 can also have folding regions 355 parallel to but not along the axis of the sleeves.

Embodiments may include one or more of the following advantages. Balloon treatment of bifurcated lumens can be facilitated by reducing the likelihood that the balloon will burst on inflation, particularly in a side branch. In addition, balloon burst, should it occur, can be made more predictable, and particularly located outside the side branch, so as to minimize engagement or snagging of a stent expanded in the side branch. The profile of the side branch balloon on deflation after angioplasty or stent delivery can be reduced, e.g. by folding or forming into a desired, predictable configuration that facilitates withdrawal from a deployed stent or body lumen. It can require less withdrawal force to remove a balloon that has been ablated from a lumen than to remove a similar balloon that has not been ablated from the same lumen.

All patents, patent applications, and publications referenced herein are incorporated by reference in their entirety.

A number of embodiments of the invention have been described. Nevertheless, it will be understood that various modifications may be made without departing from the spirit and scope of the invention. It should be understood that this disclosure is, in many respects, only illustrative. Changes may be made in details, particularly in matters of shape, size, and arrangement of steps without exceeding the scope of the disclosure. The invention's scope is, of course, defined in the language in which the appended claims are expressed.

What is claimed is:

1. A method of forming a balloon for treating a bifurcated lumen, the method comprising:
   providing a tubular parison defining an axis and having a variable wall thickness region;
   utilizing the variable wall thickness region of the tubular parison to form a balloon inflatable off the axis; and
   expanding the tubular parison to form the balloon such that a first region of the tubular parison having a greater thickness is expanded to a greater extent than a second region of the tubular parison having a lesser thickness, and in an expanded state the first region has a lesser thickness than the second region.

2. The method of claim 1 further comprising:
   forming the balloon by expanding the tubular parison in a mold shaped to correspond to a balloon inflatable off of the axis; and
   orienting the tubular parison in the mold such that the first region of the tubular parison having a greater wall thickness is expanded to a greater extent than the second region of the tubular parison having a lesser thickness.

3. The method of claim 1 further comprising forming a predefined burst region in the balloon, wherein the predefined burst region is a localized zone in which the balloon wall thickness is reduced.

4. The method of claim 1 further comprising forming a predefined folding region in the balloon, wherein the predefined folding region is a zone of increased flexibility.

* * * * *